(12) United States Patent
Raut et al.

(10) Patent No.: US 10,532,183 B2
(45) Date of Patent: Jan. 14, 2020

(54) SLEEP IMPROVEMENT DEVICE AND METHOD FOR IMPROVING SLEEP

(71) Applicant: Arenar Group B.V., Nijmegen (NL)

(72) Inventors: Samir Sopan Raut, Nijmegen (NL); Purva Samir Raut, Nijmegen (NL)

(73) Assignee: ARENAR GROUP B.V. (NL)

( * ) Notice: Subject to any disclaimer, the term of this patent is extended or adjusted under 35 U.S.C. 154(b) by 217 days.

(21) Appl. No.: 15/697,268

(22) Filed: Sep. 6, 2017

(65) Prior Publication Data

US 2019/0070386 A1 Mar. 7, 2019

(51) Int. Cl.
*A61M 21/00* (2006.01)
*A61M 21/02* (2006.01)
(Continued)

(52) U.S. Cl.
CPC ......... *A61M 21/02* (2013.01); *A61B 5/02438* (2013.01); *A61B 5/048* (2013.01); *A61B 5/0482* (2013.01); *A61B 5/0484* (2013.01); *A61B 5/4812* (2013.01); *A61B 5/4815* (2013.01); *A61B 5/6803* (2013.01); *A61B 5/6814* (2013.01); *A61B 5/6831* (2013.01); *A61B 5/7405* (2013.01); *A61B 5/01* (2013.01); *A61B 5/04014* (2013.01); *A61B 5/1116* (2013.01); *A61B 5/7455* (2013.01); *A61B 2560/0242* (2013.01); *A61B 2562/0204* (2013.01);
(Continued)

(58) Field of Classification Search
CPC ... A61M 21/00; A61M 21/02; A61B 5/02438; A61B 5/048
USPC ..................................................... 600/26–28
See application file for complete search history.

(56) References Cited

U.S. PATENT DOCUMENTS

| 10,052,452 B2 * | 8/2018 | Schoonover | A61M 21/02 |
| 2002/0005784 A1 * | 1/2002 | Balkin | A61B 5/16 340/573.1 |

(Continued)

FOREIGN PATENT DOCUMENTS

KR 2017 0028247 3/2017

OTHER PUBLICATIONS

International Search Report and Written Opinion for PCT International Patent Application Serial No. PCT/EP2018/073603, dated Dec. 12, 2018 (9 pages).
(Continued)

*Primary Examiner* — John P Lacyk
(74) *Attorney, Agent, or Firm* — Hayes Soloway P.C.

(57) ABSTRACT

A sleep improvement device and a method for improving sleep, wherein the sleep improvement device is arranged for: initiating a sleep meditation mode when the user is awake, in the sleep meditation mode emitting relaxing stimuli, monitoring the brainwave signals during a plurality of epochs, determining when the user's brainwave frequencies for at least 20 percent of one or more of the epochs are within a training range of 10 to 17 Hz and then emitting training stimuli; and initiating a dream improvement mode when one or more of the epochs are scored as a REM sleep stage and in the dream improvement mode emitting lucid dream inducing stimuli corresponding to one or more of the training stimuli from the sleep meditation mode. Also provided is a data carrier including instructions for causing the sleep improvement device to execute the method for improving sleep.

26 Claims, 7 Drawing Sheets

(51) Int. Cl.
    *A61B 5/0484*     (2006.01)
    *A61B 5/00*     (2006.01)
    *A61B 5/024*     (2006.01)
    *A61B 5/048*     (2006.01)
    *A61B 5/0482*     (2006.01)
    *A61B 5/01*     (2006.01)
    *A61B 5/04*     (2006.01)
    *A61B 5/11*     (2006.01)

(52) U.S. Cl.
    CPC ............ *A61B 2562/0219* (2013.01); *A61M 2021/0016* (2013.01); *A61M 2021/0022* (2013.01); *A61M 2021/0027* (2013.01); *A61M 2021/0044* (2013.01)

(56) References Cited

U.S. PATENT DOCUMENTS

| | | | |
|---|---|---|---|
| 2009/0131803 A1* | 5/2009 | Heneghan | A61B 5/4812 600/484 |
| 2012/0251989 A1 | 10/2012 | Wetmore et al. | |
| 2018/0154104 A1* | 6/2018 | Gerdes | A61B 5/0482 |
| 2019/0069839 A1 | 3/2019 | Park et al. | A61B 5/4815 |

OTHER PUBLICATIONS

Written Opinion for PCT International Patent Application Serial No. PCT/EP2018/073603, dated Aug. 1, 2019 (7 pages).

Erin J. Wamsley, John S. Antrobus, "The Expression of trace conditioning during non-REM sleep and its relation to subjective experience", Neurobiology of Learning and Memory 92 (2009), pp. 283-291.

V. Candas, J.P. Libert and A. Muzet, "Heating and cooling stimulations during SWS and REM sleep in man", J. terhm Biol. Vol. 7, pp. 155-158, 1982.

International Preliminary Report on Patentability for PCT International Patent Application Serial No. PCT/EP2018/073603, dated Oct. 24, 2019 (7 pages).

* cited by examiner

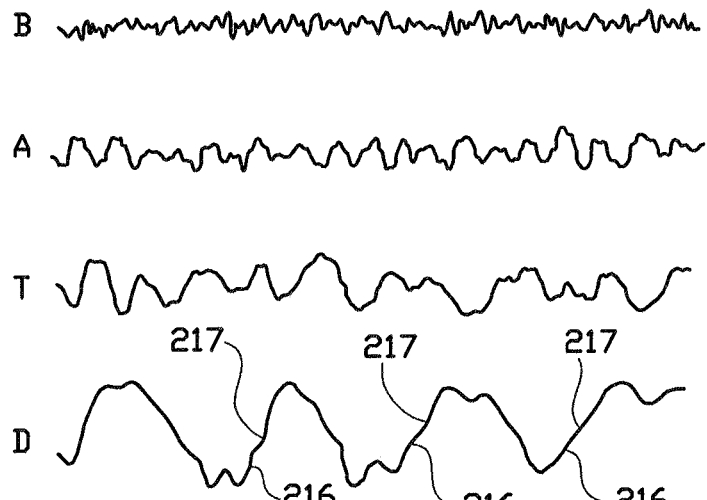
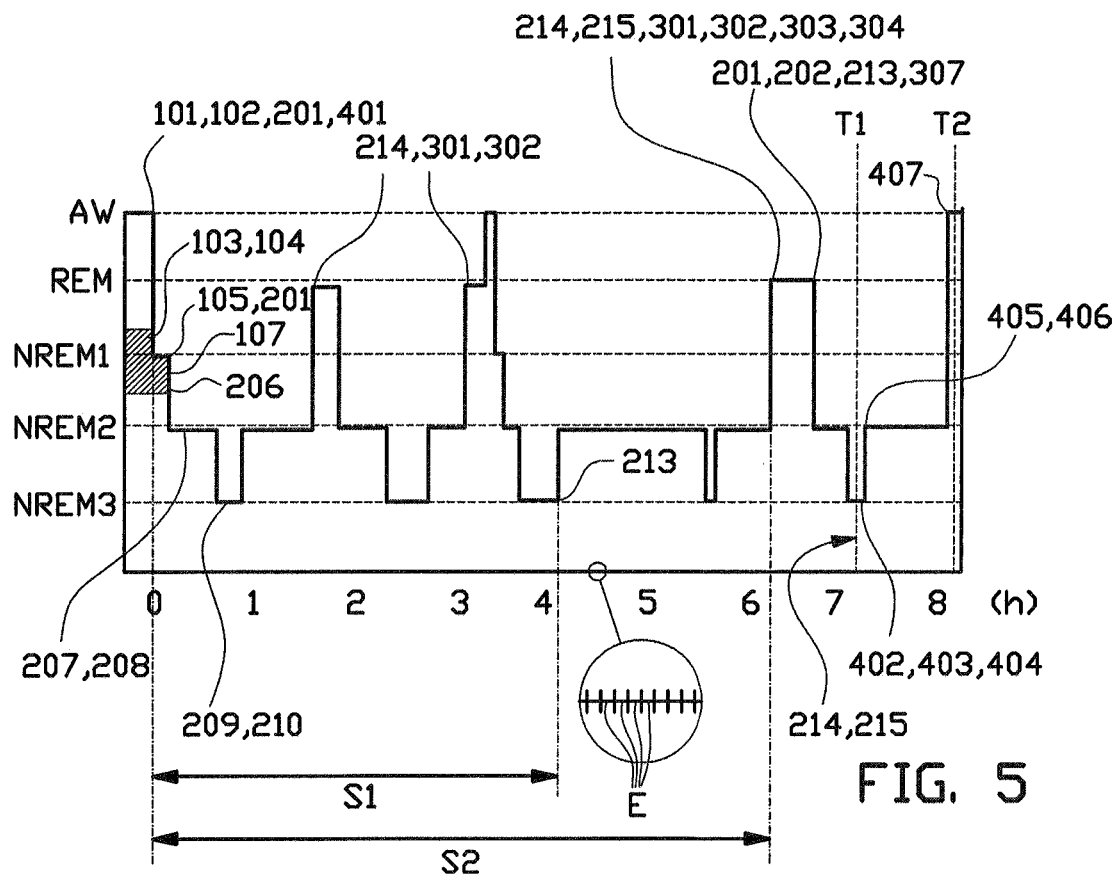

SLEEP IMPROVEMENT DEVICE AND METHOD FOR IMPROVING SLEEP

BACKGROUND

The invention relates to a sleep improvement device and a method for improving sleep.

Sleep improvement devices are known in various forms, from mobile-based apps to bedside devices and wearables. Some are directed at improving sleep quality, e.g. by providing relaxing music or a wake-up routine, while others focus on improving the dreaming experience. Dream bands in particular are designed to emit audio and visual stimuli during the Rapid Eye Movement sleep (REM sleep) in an attempt to induce lucid dreaming, a dream in which the user is aware of dreaming.

SUMMARY OF THE INVENTION

A disadvantage of the known sleep improvement devices is that the audio and visual stimuli typically only manifest themselves in the dream as very subtle cues or anomalies—if they appear at all—and are therefore very hard to identify. Hence, in practice, it may be very difficult for a user to become aware of dreaming. Moreover, when a user has poor sleeping quality, the body will try to make up for lost sleep quality by increasing the deep sleep at the expense of the REM sleep in which a state of lucid dreaming may be obtained. Hence, the REM sleep stages may be very short or may not occur at all, hence may not be enabling the user to dream in the first place. Finally, known sleep improvement devices do not address the improvement of the entire sleep cycle from going to sleep to waking up.

It is an object of the present invention to provide a sleep improvement device and a method for improving sleep that improves on at least one of the abovementioned disadvantages.

According to a first aspect, the invention provides a sleep improvement device comprising one or more brainwave sensors for detecting brainwaves of a user, one or more body vital sensors for detecting body vitals of the user and a control unit that is operationally connected to said one or more brainwave sensors and said one or more body vital sensors for receiving and processing brainwave signals and body vital signals, respectively, wherein the control unit is arranged for monitoring the brainwave signals and/or the body vital signals during a plurality of epochs and scoring sleep stages for each epoch, wherein the sleep improvement device is further provided with one or more stimulus emitters operationally connected to and controlled by the control unit, wherein the control unit is arranged for:

initiating a sleep meditation mode when the user is awake, wherein in said sleep meditation mode the control unit is arranged for controlling one or more of the one or more stimulus emitters to emit relaxing stimuli, monitoring the brainwave signals during each epoch, determining when the user's brainwave frequencies for at least 20 percent of one or more of the epochs are within a training range of 10 to 17 Hz and then controlling one or more of the one or more stimulus emitters to emit training stimuli; and initiating a dream improvement mode when the control unit has scored one or more of the epochs as a REM sleep stage, wherein in said dream improvement mode the control unit is arranged for controlling one or more of the one or more stimulus emitters to emit lucid dream inducing stimuli corresponding to one or more of the training stimuli from the sleep meditation mode.

Although prior art devices are known to provide lucid dream inducing stimuli during the REM sleep stages, it can be very difficult for an inexperienced user to recognize or identify these lucid dream inducing stimuli. It is like trying to understand a language without knowing the words. The stimuli would be meaningless and may not appear as a part of the dream. By providing the learning stimuli in the training range the user can be trained to identify or recognize the training stimuli as they would appear as anomalies or cues in a dream, thereby significantly increasing the chances of user becoming aware of dreaming during the dream improvement mode, when the lucid dream inducing stimuli corresponding to one or more of the training stimuli are emitted. Optionally the user can even associate said cues with the dream that the user wants to experience, thereby setting the dream intention. It has been found that training stimuli can be particularly effective when the cues are the last thing remembered by the user before drowsing off and eventually falling asleep. Hence, the training range is chosen as the phase in which the user starts slipping from awake into the NREM1 sleep stage.

In a preferred embodiment, the training range is 12 to 17 Hz. More preferably the training range is 13 to 16 Hz. By choosing a smaller training range, the training stimuli can be emitted more accurately in the phase in which the user starts slipping from awake into the NREM1 sleep stage.

In a further embodiment of the sleep improvement device, the control unit is arranged for initiating a sleep improvement mode when the control unit has scored one or more of the epochs as a NREM1 sleep stage, wherein in said sleep improvement mode the control unit is arranged for controlling one or more of the one or more stimulus emitters to emit sleep inducing stimuli. The sleep improvement mode can improve the quality of the sleep by pulling the user into a deeper sleep stage and keeping the user in said sleep stage for a longer period of time. By improving the sleep quality, the user also has a greater chance of enhancing the REM sleep stage in which lucid dreaming can be attained.

Preferably, the sleep inducing stimuli comprise brainwave entrainment stimuli, more preferably binaural beats. Brainwave entrainment stimuli are stimuli of periodic nature, mostly audio, visual or tactile, that can use the brain's ability to naturally synchronize its brainwave frequencies to these stimuli. An example of brainwave entrainment stimuli are binaural beats or periodic vibrations. Hence, the user can be pulled towards or kept at a certain brainwave frequency corresponding to the frequency of the binaural beats. Preferably, the relaxing stimuli are maintained to mask the brainwave entrainment stimuli, which alone could become annoying for the user.

In a preferred embodiment the control unit is arranged for fading out or turning off the relaxing stimuli when the control unit has scored one or more of the epochs as a NREM2 sleep stage. The effectiveness of the relaxing stimuli gradually diminishes as the user continues to fall deeper and deeper into NREM3 sleep stage from the NREM2 sleep stage.

In a further embodiment the control unit is arranged for controlling one or more of the one or more stimulus emitters to introduce white noise when the control unit has scored one or more of the epochs as a NREM3 sleep stage. The white noise can effectively mask distracting sounds, thereby ensuring a longer period of sound sleep.

In a preferred embodiment thereof, the control unit is provided with a deep sleep timer that adds up a deep sleep time of the epochs that are scored as a NREM3 sleep stage, wherein the control unit is arranged for fading out or turning off the sleep inducing stimuli when the control unit has determined that a predefined minimum deep sleep time has been reached. Extending NREM3 sleep stages of the user in the early parts of the sleep cycle with the sleep inducing stimuli can make REM sleep stages in the later parts of the sleep cycle more frequent, longer and/or more consistent. The minimum deep sleep timer can ensure that the user gets an optimum NREM3 sleep and thereby also optimum REM sleep.

Additionally or alternatively, the control unit is arranged for introducing the white noise only after the predefined minimum deep sleep time has been reached. By providing the white noise after expiry of a minimum deep sleep time, it can be ensured that the white noise is most effective.

In a further embodiment, in the NREM3 sleep stages, the user predominantly has brainwaves in the Delta frequency spectrum, wherein in said sleep improvement mode, the control unit is arranged for recognizing a rising slope of a Delta brainwave and for controlling one or more of the one or more stimulus emitters to emit amplitude enhancing stimuli during said rising slope. The amplitude enhancing stimuli can improve the amplitude of the brainwaves in the Delta spectrum, which is believed to further enhance the deep sleep, and—in combination with a good REM sleep—could improve memory consolidation. Preferably, the amplitude enhancing stimuli comprise short audio stimuli or tactile stimuli. It has been found that such short stimuli cause an increase in the amplitude of the brainwaves in the Delta spectrum.

In a preferred embodiment, the control unit is provided with a sleep timer that adds up sleep time that the user is asleep from the first epoch that is scored as a NREM1 sleep stage, wherein the control unit is arranged for emitting the lucid dream inducing stimuli only after a predefined minimum sleep time has been reached. Hence, some of the early REM sleep stages could be skipped to ensure that the user has at least had a predefined minimum sleep time before starting to experiment with lucid dream inducing stimuli.

In another embodiment the control unit is arranged for determining the brainwave frequencies of the user at the start of the sleep meditation mode and/or when the user was still awake, wherein in the dream improvement mode the control unit is arranged for detecting bursts of brainwave frequencies higher than the brainwave frequencies detected at the start of the sleep meditation mode and/or when the user was still awake. This can be an indication that the user has attained lucid dreaming.

When said bursts of high brainwave frequencies are detected, it is preferred that the control unit is arranged to control the one or more stimulus emitters to stop emitting the lucid dream inducing stimuli. By stopping the lucid dream inducing stimuli, the user can continue with the lucid dream without being distracted by further lucid dream inducing stimuli.

In another embodiment the control unit is programmed with a wake up window having a start time and an end time, wherein the control unit is arranged for initiating a wake up mode when the start time has been reached, wherein in said wake up mode the control unit is arranged for determining the sleep stage score of the last epoch and for controlling one or more of the one or more stimulus emitters to emit alarm stimuli when the last epoch is scored as a NREM2 sleep stage or when the end time has been reached. By setting a wake up window, the user can be woken up at an appropriate time within said wake up window, in particular when the user is in the NREM2 sleep stage. When waking up from the NREM2 sleep stage, the user can feel rejuvenated and/or a groggy feeling can be prevented.

In a further embodiment the one or more stimulus emitters comprises one or more stimulus emitters from the group comprising visual stimulus emitters, audio stimulus emitters, tactile stimulus emitters and olfactory stimulus emitters. These stimulus emitters, and preferably a combination thereof, can provide an immersive experience of stimuli that can be more easily associated with specific scenarios, thereby allowing the user to set clear dream cues and a clear dream intention.

In a further embodiment the one or more body vital sensors comprises one or more body vital sensors from the group comprising a body movement sensor, a heart rate sensor and a body temperature sensor. The body vital signals from these body vital sensors can be used to more accurately determine the sleep stage of the user based on body vitals characteristic for the different sleep stages. By using the brainwave sensors in combination with the body vital sensors, the chances of false identification of sleep stages can be reduced.

In a further embodiment the one or more stimulus emitters comprise a left speaker and a right speaker which are arranged to be placed at or near the user's left ear and right ear, respectively, and wherein the one or more body vital sensors comprises a body movement sensor, wherein the control unit is arranged for tracking the user's head position based on the body vital signals from the body movement sensor and for adjusting the volume of the left speaker and the right speaker based on the user's head position. When the user lies on one side, the audio stimuli from one of the speakers are typically experienced to be louder than the audio stimuli from the other speaker. By adjusting the volume based on the user's head position, the volume balance as experienced by the user can be improved.

In a further embodiment the sleep improvement device is provided with a communication module to connect to one or more smart external devices that control the ambient conditions, wherein the control unit is arranged for controlling one or more of said smart external devices to adjust the ambient conditions based on the brainwave signals from the one or more brainwave sensors and/or the body vital signals from the one or more body vital sensors. This enables the sleep improvement device to create a conducive environment for sleep improvement.

According to a second aspect, the invention provides a method for improving sleep using the sleep improvement device according to any one of the aforementioned device embodiments, wherein the method comprises the steps of:
 initiating a sleep meditation mode when the user is awake, in said sleep meditation mode emitting relaxing stimuli, monitoring the brainwave signals during each epoch, determining when the user's brainwave frequencies for at least 20 percent of one or more of the epochs are within a training range of 10 to 17 Hz and then emitting training stimuli; and
 initiating a dream improvement mode when one or more of the epochs are scored as a REM sleep stage and in said dream improvement mode emitting lucid dream inducing stimuli corresponding to one or more of the training stimuli from the sleep meditation mode.

The method and its respective embodiments relate to the practical implementation of the aforementioned sleep improvement device and thus have the same technical advantages which will not be repeated hereafter for reasons of conciseness.

In an embodiment the method further comprises the steps of initiating a sleep improvement mode when one or more of the epochs are scored as a NREM1 sleep stage and in said sleep improvement mode emitting sleep inducing stimuli.

In a further embodiment the method further comprises the step of introducing white noise when one or more of the epochs are scored as a NREM3 sleep stage.

In the NREM3 sleep stages, the user predominantly has brainwaves in the Delta frequency spectrum. In a further embodiment the method further comprises the step of emitting amplitude enhancing stimuli during a rising slope of a Delta brainwave.

In another embodiment the method further comprises the steps of setting a wake up window having a start time and an end time, initiating a wake up mode when the start time has been reached, in said wake up mode determining the sleep stage score of the last epoch and emitting alarm stimuli when the last epoch is scored as a NREM2 sleep stage or when the end time has been reached.

In yet another embodiment the method comprises the step of adjusting the ambient conditions based on the brainwaves and/or body vitals of the user.

According to a third aspect, the invention provides a data carrier comprising instructions for causing the sleep improvement device according to any one of the aforementioned device embodiments to execute the method according to any one of the aforementioned method embodiments. Hence, a data carrier like a data stream, a storage medium or computer program product can effectively cause the sleep improvement device to execute the aforementioned method, thereby obtaining the same technical advantages as in the previously discussed embodiments.

The various aspects and features described and shown in the specification can be applied, individually, wherever possible. These individual aspects, in particular the aspects and features described in the attached dependent claims, can be made subject of divisional patent applications.

BRIEF DESCRIPTION OF THE DRAWINGS

The invention will be elucidated on the basis of an exemplary embodiment shown in the attached schematic drawings, in which:

FIG. 4 shows exemplary brainwaves;

FIG. 5 shows an exemplary sleep cycle; and

DETAILED DESCRIPTION OF THE INVENTION

Figure 1:
FIG. 1 shows a sleep improvement device 1 according to the invention, worn by a user.
Figure 2:
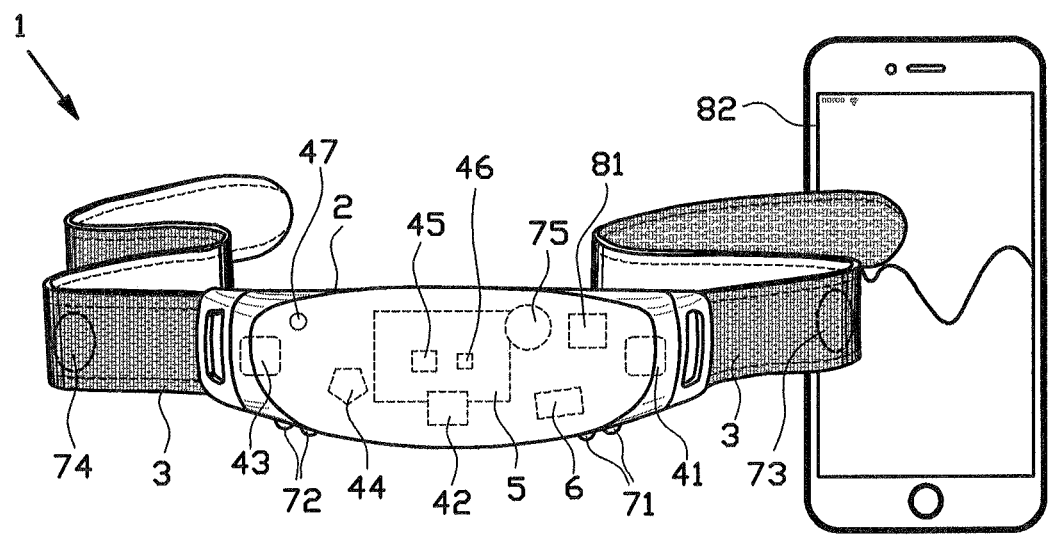
FIG. 2 shows a front view of the sleep improvement device 1 according to FIG. 1 and an external smart device connected wirelessly to the sleep improvement device.
Figure 3:
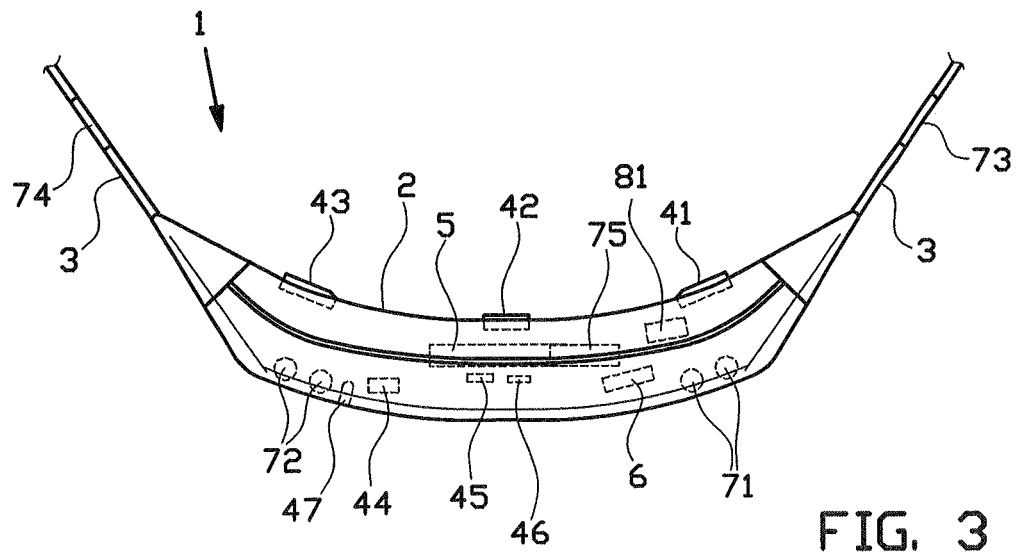
FIG. 3 shows a top view of the sleep improvement device 1 according to FIG. 1.

FIGS. 1, 2 and 3 show a sleep improvement device 1 according to an exemplary embodiment of the invention. Sleep and dreams play an important role in health and happiness. Sleep rejuvenates the body while dreams rejuvenate the mind. The quality of sleep can also have a significant effect on memory consolidation. The sleep improvement device 1 according to the invention is arranged for improving on one or more aspects of sleep, including—but not limited to—quality of sleep, dreaming, memory consolidation and waking up.

The sleep improvement device 1 in this example is a wearable device, e.g. in the form of a band that can be strapped to a user's head 9. As shown in FIG. 1, the sleep improvement device 1 comprises a housing 2 for holding electronics and a support 3 for supporting the housing 2 relative to a user's head 9. In this exemplary embodiment, the support 3 is a flexible band, preferably a fabric band, that is arranged to be strapped or wrapped around the user's head and fastened with a suitable fastener, preferably in an adjustable manner, e.g. with the use of Velcro. Alternative, the support 3 can be any other type of element that is ergonomically adapted to be worn on the head, e.g. an adhesive tape or a cap.

As schematically shown in FIGS. 2 and 3, the electronics comprise one or more brainwave sensors 41, 42, 43 for detecting neural oscillations or brainwaves of the user, a control unit 5, e.g. a microcontroller, various circuitry or a combination thereof, that is operationally connected to the one or more brainwave sensors 41, 42, 43 for receiving and processing brainwave signals representative of the measured brainwaves from the one or more brainwave sensors 41, 42, 43 and a memory 6 for storing the processed signals, audio files and other relevant sleep data. In this exemplary embodiment, the sleep improvement device 1 comprises three non-invasive brainwave sensors 41, 42, 43 in the form of strategically placed Electroencephalography (EEG) electrodes that are arranged to be in direct, dry contact with the user's head 9. Preferably, at least one of the electrodes is placed on the forehead of the user's head 9 for brainwave measurement. Optionally, the sleep improvement device 1 may further be provided with one or more body vital sensors of the group comprising a body movement sensor 44, preferably an accelerometer, for measuring the user's head movements, a heart rate sensor 45 for measuring the user's heart rate, a body temperature sensor 46 for measuring the user's body temperature and a microphone 47 for detecting ambient sound. The control unit 5 is operationally connected to said one or more body vital sensors—if provided—for receiving and processing the body vital signals thereof.

As further shown in FIGS. 2 and 3, the sleep improvement device 1 comprises one or more stimulus emitters 71-75 of the group comprising a visual stimulus emitter 71, 72, an audio stimulus emitter 73, 74 and a tactile stimulus emitter 75 for emitting relaxing stimuli, training stimuli, sleep inducing stimuli, lucid dream inducing stimuli, amplitude enhancing stimuli and/or alarm stimuli—as explained hereafter—to the user during sleep. The one or more stimulus emitters 71-75 are operationally connected to and controlled by the control unit 5.

In this exemplary embodiment, the sleep improvement device 1 comprises two visual stimulus emitters 71, 72 in the form of a first light source 71 and a second light source 72 which are strategically placed to emit or cast visual stimuli, e.g. light of different colors and/or blink frequencies, onto left eye and the right eye, respectively, of the user. The light sources 71, 72 preferably comprise one or more Light Emitting Diodes or LEDs, preferably RGB LEDs, which are arranged to emit different colors of light and/or blink frequencies based on the user's preferences. The sleep improvement device 1 further has two audio stimulus emitters 73, 74 in the form of a first speaker 73 and a second speaker 74 connected to or integrated into the support 3 at or near the user's left ear and right ear, respectively, for emitting audio stimuli, e.g. sounds. In this example, the sleep improvement device 1 has a tactile stimulus emitter 75 in the form of a vibration motor 75 strategically located in the housing 2 to emit tactile stimuli, e.g. vibrations, through said housing 2 onto the head 9 of the user.

Optionally, the sleep improvement device 1 may include a further odor or olfactory stimulus emitter (not shown) for emitting odor or olfactory stimuli, e.g. the aroma of fresh cut grass.

Preferably, all of the aforementioned operational components of the sleep improvement device 1 are contained onboard in the wearable device. The sleep improvement device 1 can therefore be considered as a standalone device, i.e. a device that can operate autonomously. Alternatively, some components can be located outside of the wearable device and may be connected by wire or wirelessly.

FIG. 2 schematically shows that the sleep improvement device 1 is provided with a communication module 81 to connect by wire and/or wirelessly to one or more external smart devices 82, e.g. a smartphone or smart home applications. In this example, the sleep improvement device 1 is provided with a Bluetooth module 81 to communicate wirelessly with the one or more external smart devices 82. Examples of externally located components may be pillow speakers, wireless speakers, wake-up lights, the odor stimulus emitter and wake up alarms. In an optional embodiment, the sleep improvement device 1 may be connected further to one or more external smart devices 82 that control the ambient conditions, e.g. to smart home systems, smart lighting, smart mattress, smart scented candles or a smart thermostat. The control unit 5 is arranged for controlling one or more of said smart external devices 82 based on the signals from the one or more brainwave sensors 41-43 and/or the one or more body vital sensors 44-46 to set, adjust and/or optimize the ambient conditions and/or to create a conducive environment for sleep improvement.

One of the external smart devices 82 may be provided with an app to store historical data from the one or more sensors and/or to present said historical data to the user. Said app may also be used for configuring the sleep improvement device 1. Said external smart device 82 is typically connected to the internet and thus enables communication between the app and a centralized server, e.g. for storage and/or cloud computing purposes.

A method for improving sleep with the use of the aforementioned sleep improvement device 1 will be elucidated below with reference to FIGS. 4-9.

FIG. 4 shows exemplary brainwaves of the user with Beta brainwaves B, Alpha brainwaves A, Theta brainwaves T and Delta brainwaves D.

FIG. 5 shows a graph of an exemplary sleep cycle of a user to illustrate the operation of the sleep improvement device 1. The horizontal axis of the graph shows the time in hours. The vertical axis of the graph shows the five stages of sleep, being: awake (AW), Rapid Eye Movement (REM) or dream sleep, first stage Non-rapid Eye Movement (NREM1) or drowsy stage, second stage Non-Rapid Eye Movement (NREM2) or light sleep stage and third stage Non-Rapid Eye Movement (NREM3) or deep sleep stage.

By using the brainwave signals from one or more of the one or more brainwave sensors 41, 42, 43, the control unit 5 can easily and accurately determine the NREM1, NREM2 and NREM3 sleep stages. The REM sleep stages can be accurately distinguished from awake by processing and analyzing the combination of the brainwave signals from one or more of the one or more brainwave sensors 41, 42, 43 and the body vital signals from one or more of the one or more body vital sensors 44, 45, 46. Said signals from the one or more body vital sensors 44, 45, 46 can also be used to prevent false identification of the NREM1, NREM2 and NREM3 sleep stages.

In particular, the control unit 5 is arranged for analyzing the brainwave frequencies and body vital signals during epochs E of a predefined time (as schematically shown in the detail of FIG. 5 at the horizontal axis), e.g. 30 seconds, and for scoring or classifying said epochs E based on said analysis. Time of a certain sleep stage is scored for each epoch E starting with the first epoch E that is acquired. If two or more sleep stages occur in one epoch E, the score of said epoch E is assigned with the sleep stage that was dominant during said epoch E.

The sleep stages are characterized by the following brainwave parameters (see Table 1):

TABLE 1

(according to the American Academy of Sleep Medicine)

| Stage | Brainwave parameters |
|---|---|
| AW | Low amplitude mixed frequency EEG pattern<br>When eyes are open, predominant low amplitude Beta brainwaves (>13 Hz) and may be accompanied by Alpha brainwaves (8-13 Hz) |
| REM | Low amplitude mixed frequency EEG pattern<br>Mostly no sleep spindles or K-complexes<br>Predominant Theta brainwaves (4-8 Hz) and Beta brainwaves (13-30 Hz)<br>May contain Alpha brainwaves (1-2 Hz slower than in AW stage)<br>May contain Sawtooth waves (2-6 Hz) serrated bursts of activity |
| NREM1 | Low amplitude mixed frequency EEG pattern<br>More than 50% of epoch consists of Theta brainwaves (4-8 Hz) mostly accompanied by Alpha brainwaves (8-13 Hz) |
| NREM2 | Predominant Theta brainwaves (4-8 Hz) with scattered sleep spindles and/or K-complexes<br>Sleep spindles are high frequency bursts in the range of 11-16 Hz (most commonly 12-14 Hz) that last for >=0.5 Seconds<br>K-complexes are high amplitude sharp waves that stand out from the background signal and last for >=0.5 Seconds |
| NREM3 | Predominant Delta brainwaves (<4 Hz)<br>More than 20% of epoch consists of high amplitude slow Delta brainwaves (<2 Hz) |

The sleep stages can be further distinguished by the following characteristic body vitals (see Table 2):

TABLE 2

| Stage | Body vitals |
|---|---|
| AW | Active body movements |
| REM | Increased eye movement<br>Increased heart rate that may have an irregular rhythm<br>Increased body temperature<br>Body paralyzed |
| NREM1 | Reduced body movements<br>Slowing heart rate with a regular rhythm |

TABLE 2-continued

| Stage | Body vitals |
|---|---|
| NREM2 | Slowing heart rate with a regular rhythm<br>Decreasing body temperature |
| NREM3 | Slowed heart rate with a regular rhythm<br>Decreased body temperature |

Figure 8:
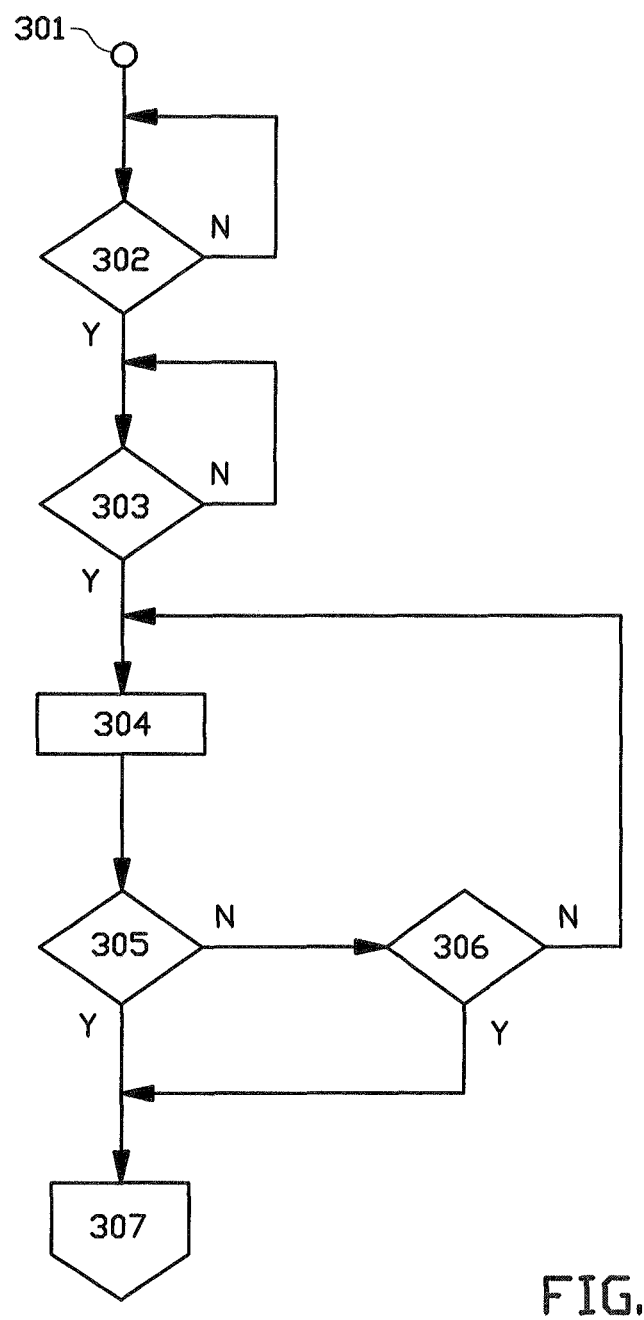
Figure 9:
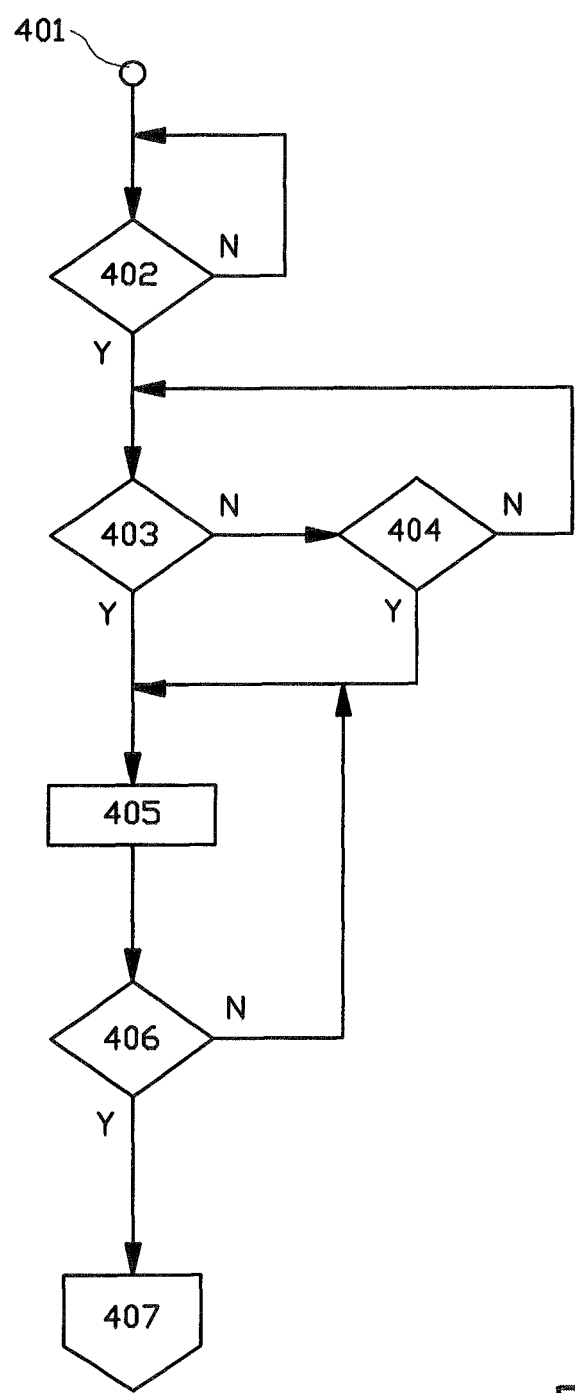

During the method according to the invention, the sleep improvement device 1 operates in one or more modes of the group comprising a sleep meditation mode (FIG. 6), a sleep improvement mode (FIG. 7), a dream improvement mode (FIG. 8) and a wake up mode (FIG. 9). The sleep improvement device 1 is switched between said modes based on the scoring of the epochs E.

Figure 6:
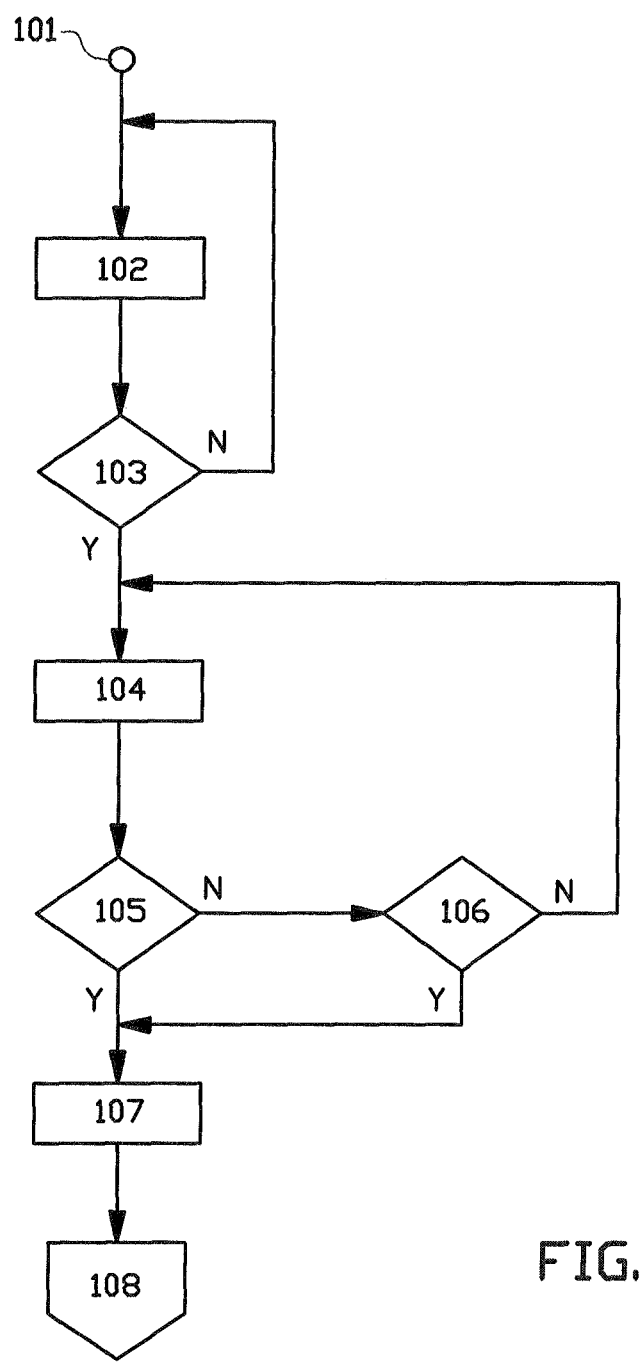
FIGS. 6, 7, 8 and 9 show flow charts of a sleep meditation mode, a sleep improvement mode, a dream improvement mode and a wake up mode, respectively.

FIG. 6 shows a flow chart of the operation of the sleep improvement device 1 during sleep meditation mode. In the sleep meditation mode, training stimuli are emitted to train the user to identify or recognize the training stimuli as they would appear as anomalies or cues in a dream, thereby significantly increasing the chances of user becoming aware of dreaming during the dream improvement mode, when lucid dream inducing stimuli corresponding to one or more of the training stimuli are emitted. A routine of lucid dream inducing stimuli may be provided as default or may have been setup previously by the user and can be fine-tuned to optimize the effectiveness.

As shown in FIG. 6, the sleep meditation mode is initiated when the user is still awake and intends to go to sleep (step 101). Preferably, the brainwave frequencies of the user at the start of the sleep meditation mode are stored in the memory (6) for later use in the dream improvement mode. The sleep meditation mode starts with the sleep improvement device 1 emitting relaxing stimuli through one or more of its one or more stimulus emitters 71-75 (step 102). In this particular example, the control unit 5 controls the audio stimulus emitters 73, 74, i.e. the speakers 73, 74, to play music that helps the user to relax. Optionally, the type of music, the rhythms, the tempo and/or volume of the music may be adjusted in response to signals from the one or more brainwave sensors 41, 42, 43 and/or the one or more body vital sensors 44, 45, 46 to optimally match the music to the sleep stage of the user. The optional microphone 47 can be used to sense the ambient sound levels and adjust the relaxing stimuli accordingly.

The one or more brainwave sensors 41, 42, 43 continue to detect the brainwave frequencies and send signals representative of said brainwave frequencies to the control unit 5 for processing. The control unit 5 continues to monitor the brainwave signals during each epoch E and determines when the user's brainwave frequency has dropped below 17 Hertz (Hz) and preferably below 16 Hz for at least 20 percent, preferably at least 40 percent, of one the epochs E (step 103). Said epoch E is representative of a phase in which the user starts slipping from awake into the NREM1 sleep stage and is about to fall asleep. It is during this phase, when the brainwave frequencies are within a training range of 10 to 17 Hz, preferably 12 to 17 Hz and most preferable 13 to 16 Hz for at least 20 percent, preferably at least 40 percent, of one of the epochs E, that the control unit 5 starts to control the one or more stimulus emitters 71-75 to emit the one or more training stimuli (step 104). Prior to or during the sleep meditation mode, the user is given instructions to consciously remember the cues caused by the training stimuli and optionally to associate said cues with the dream that the user wants to experience, thereby setting the dream intention. The user may for example associate a certain blinking light or vibration pattern with a dream about flying. The sleep meditation mode will be most effective for inducing a lucid dream when these cues are the last thing remembered by the user before drowsing off and eventually falling asleep.

The sleep improvement device 1 continues to emit the training stimuli at least until the control unit 5 has scored one or more of the epoch E as a NREM1 sleep stage (step 105) or when a predetermined or preprogrammed sleep meditation timer has run out (step 106). The control unit 5 then fades out or turns off the training stimuli (step 107) and ends the sleep meditation mode (step 108). The sleep meditation timer can be set at only a few minutes, e.g. at less than five minutes or less than three minutes, which is sufficient to effectively imprint cues into the brain that will appear as anomalies in the dream.

Figure 7:
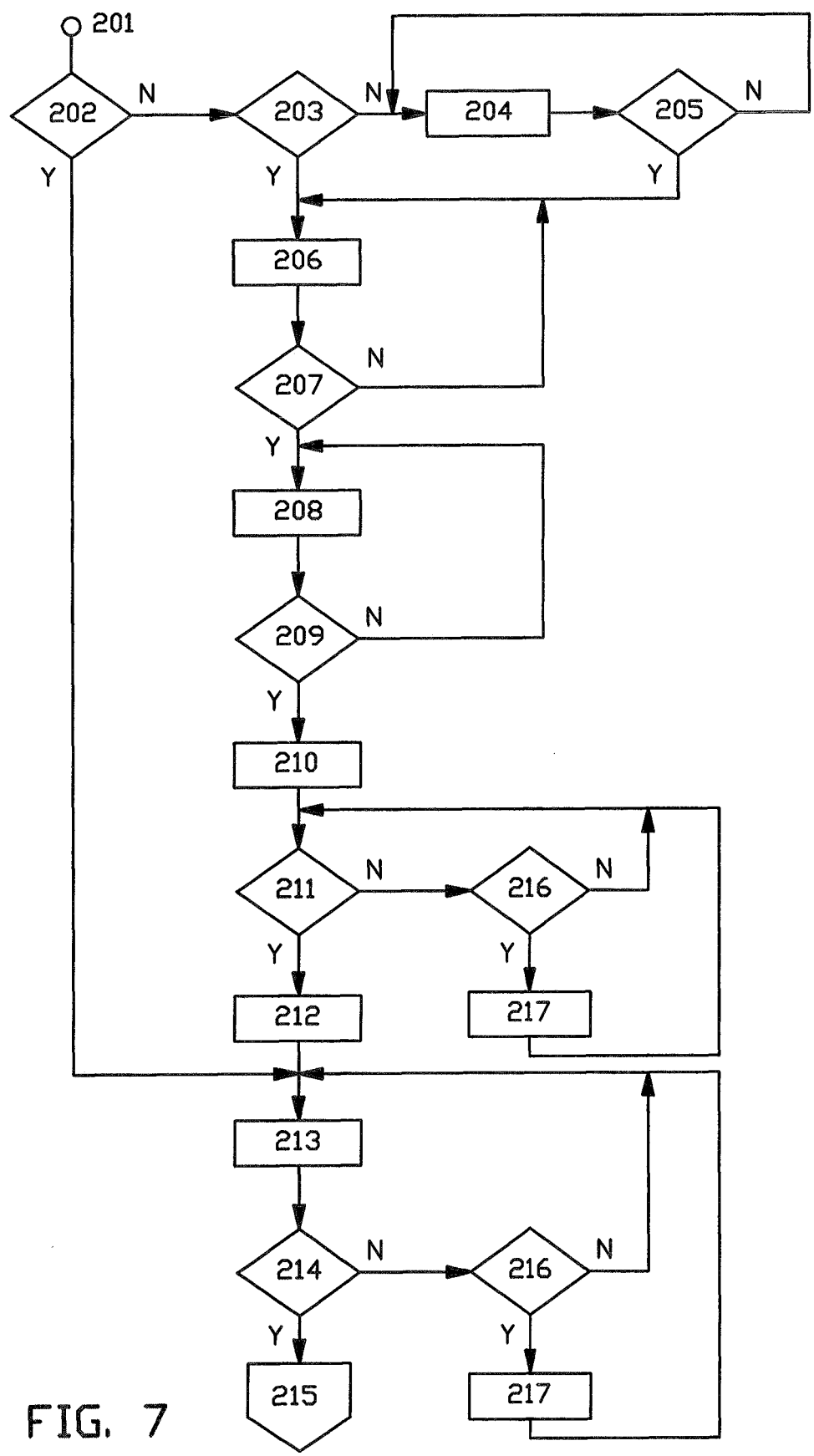

FIG. 7 shows a flow chart of the sleep improvement mode. In this exemplary embodiment, the sleep improvement mode is preceded by the aforementioned sleep meditation mode. The sleep improvement mode may also be initiated independently from the sleep meditation mode, e.g. when the intention is solely to improve the quality of the sleep. The goal of the sleep improvement mode is to pull the user from the NREM1 sleep stage into the NREM2 sleep stage and subsequently into the NREM3 sleep stage and further to improve on the quality of said sleep stages.

As shown in FIG. 7 the sleep improvement mode can be initiated automatically following the sleep meditation mode (FIG. 6) or the dream improvement mode (FIG. 8, as explained hereafter). Alternatively, the user may consciously choose to initiate the sleep improvement mode without the sleep meditation mode and/or the dream improvement mode, e.g. when the sole purpose is to improve sleep.

When the sleep improvement mode is initiated (step 201), the control unit 5 first checks whether the sleep improvement mode is initiated at the end of the dream improvement mode (step 202). When this is the case, the control unit 5 goes directly to step 213, as will be explained below. When this is not the case, the control unit 5 then checks whether the sleep improvement mode is initiated at the end of the sleep meditation mode (step 203). When this is the case, the control unit 5 goes directly to step 206, as will be explained below. When the sleep improvement mode is not preceded by the dream improvement mode or the sleep meditation mode, it is initiated immediately with the control unit 5 going through a cycle of providing relaxing stimuli (step 204), similar to step 102 in FIG. 6, and determining if the user has entered the NREM1 sleep stage (step 205), similar to step 105 in FIG. 6. When the user is in the NREM1 sleep stage, the control unit 5 goes to step 206.

Alternatively, the sleep improvement mode may simply start at the end of the sleep meditation mode, starting from step 206 as explained below.

As the relaxing stimuli and/or the training stimuli from the sleep meditation mode continue, the control unit 5 controls one or more of the one or more stimulus emitters 71-75 to emit sleep inducing stimuli (step 206), e.g. brainwave entrainment stimuli that have frequencies in the frequency spectrums of the NREM1, NREM2 and NREM3 sleep stages to pull the user further into said sleep stages. The brainwave entrainment stimuli use the brain's ability to naturally synchronize its brainwave frequencies to external visual, audio or tactile stimuli of periodic nature. In this example, the control unit 5 controls the audio stimulus emitters 73, 74, e.g. the speakers 73, 74, to emit an auditory illusion at a frequency that equals the predominant brainwave frequency at which the brain currently is or to which the brain should adapt. The auditory illusion can be a binaural beat, an illusionary tone that is registered by the brain when confronted with tones with different frequencies between the left ear and the right ear, respectively, e.g. an illusionary sinusoidal wave of 5 Hz when a sinusoidal wave of 200 Hz is presented to the left ear and a sinusoidal wave of 205 Hz is presented to the right ear. Alternatively, the brainwave entrainment stimuli may comprise periodic vibrations. The sleep inducing stimuli are preferably superimposed over the relaxing stimuli from the sleep meditation mode.

The sleep inducing stimuli may be adjusted continuously in response to signals from the one or more brainwave sensors 41, 42, 43 and/or the one or more body vital sensors 44, 45, 46 to match the sleep stage of the user. The optional microphone 47 can be used to sense the ambient sound levels and adjust the sleep inducing stimuli accordingly.

The sleep inducing stimuli can prevent the user from waking up and can pull the user further into the deeper sleep stages. The control unit 5 continues to monitor the brainwave frequencies during each epoch E and scores each epoch E based on the signals from the one or more brainwave sensors 41, 42, 43 and/or the body vital signals from the one or more body vital sensors 44, 45, 46 and is arranged for determining when one of the epochs E has the frequency range and/or has body vitals characteristic of the NREM2 sleep stage (step 207). The control unit 5 is then arranged for fading out, turning off or cancelling the relaxing stimuli and/or the training stimuli, which are now superfluous (step 208).

The control unit 5 continues to monitor the brainwave frequencies during each epoch E and scores each epoch E based on the signals from the one or more brainwave sensors 41, 42, 43 and/or the body vital signals from the one or more body vital sensors 44, 45, 46 and is arranged for determining when one or more of the epochs E have the frequency range and/or has body vitals characteristic of the NREM3 sleep stage (step 209). When one or more of the epochs E are scored as a NREM3 sleep stage, the control unit 5 is arranged for completely turning off or cancelling the relaxing stimuli (step 210). The control unit 5 is provided or programmed with a deep sleep timer that adds up a deep sleep time of the epochs E that are scored as a NREM3 sleep stage. The control unit 5 checks whether the deep sleep timer has reached a predefined minimum deep sleep time S1, as shown in FIG. 5 (step 211). This minimum deep sleep time S1 can be set by the user or can be adjusted by the control unit 5 based on analysis of previously logged sleep data. The deep sleep time may for example be set at a minimum time in the NREM3 sleep stage of 1 hour. When said deep sleep time S1 has not been reached, the control unit 5 will maintain the sleep inducing stimuli (step 206). When the minimum deep sleep time S1 has been reached, the control unit 5 is arranged for fading out or turning off the sleep inducing stimuli (step 212). The control unit 5 then controls the audio stimulus emitters 73, 74, e.g. the speakers 73, 74, to gently introduce white noise that masks distractions in the later parts of the sleep cycle to ensure a longer duration of sound sleep (step 213). White noise is a random audio signal having equal intensity at different frequencies. The white noise has the same effect as a continuously humming ventilation fan or of a car engine. The optional microphone 47 can be used to sense the ambient sound levels and adjust the volume of the white noise accordingly to mask said sound levels.

The sleep inducing stimuli ensure that the user actually reaches the NREM3 sleep stage and gets the minimum deep sleep. The white noise promotes a longer duration of sound sleep. Hence, the sleep improvement mode can significantly enhance the NREM3 sleep stage, and thus the deep sleep. Moreover, the improved NREM3 sleep stages are beneficial to the REM sleep stages, which are typically more prominent towards the end of the sleep cycle. When the overall sleeping quality is bad, the body will try to make up for lost sleep quality by increasing the NREM3 sleep stage first at the expense of the REM sleep stage. Hence, when the overall sleeping quality is sufficient, the occurrence of the REM sleep stages will be more frequent, longer and/or more consistent.

The control unit 5 continues to monitor the brainwave frequencies during each epoch E and scores each epoch E based on the signals from the brainwave sensors 41, 42, 43 and/or the body vital signals from the one or more body vital sensors 44, 45, 46. The control unit 5 is arranged for maintaining the white noise at least until one of the epochs E is scored as a REM sleep stage (step 214) or when the wake up mode is initiated (see FIG. 9). The control unit 5 then ends the sleep improvement mode and stops the white noise (step 215). Optionally, the control unit 5 is provided with a sleep timer, similar to the deep sleep timer, that can be used to check if the sleep improvement mode should end. The sleep timer is arranged to add up a sleep time of the epochs E that are scored as REM, NREM1, NREM2 or NREM3 sleep stages from the first epoch E that was scored as a NREM1 sleep stage. The control unit 5 may stay within the sleep improvement mode if a minimum sleep time S2, as shown in FIG. 5, has not been reached. This minimum sleep time S2 can be set by the user or can be adjusted by the control unit 5 based on analysis of previously logged sleep data. The minimum sleep time S2 may for example be set to 6 hours from the moment that the first epoch E that was scored as a NREM1 sleep stage. If said minimum sleep time S2 has not yet been reached, the control unit 5 will continue with the sleep improvement mode as if the REM sleep stage has not been reached, i.e. it will continue to emit the white noise (step 213).

During the NREM3 sleep stage, the user's brainwaves are predominantly in the Delta frequency spectrum, as shown in FIG. 4. Said Delta waves have a relatively high amplitude, e.g. for a young adult typically in the range of 100-200 microvolts or even higher. An optimal amplitude may result in an enhanced deep sleep, which—in combination with a good REM sleep—could improve memory consolidation. Elderly people in particular have a lower than normal amplitude. In a preferred embodiment of the invention, the control unit 5 is arranged for recognizing a rising slope of a Delta wave (step 216). When a rising slope is detected, the control unit 5 is arranged for controlling one or more of the one or more stimulus emitters 71-75 to emit amplitude enhancing stimuli (step 217). The amplitude enhancing stimuli may be in the form of short audio stimuli or tactile stimuli, e.g. short sound and/or vibrations, to promote the rise of said Delta wave and thereby amplifying the amplitude of said Delta wave. Preferably, the amplitude enhancing stimuli are provided together with the sleep inducing stimuli and/or together with the white noise, e.g. between steps 210 and 211 and/or between steps 212 and 213.

FIG. 8 shows a flow chart of the dream improvement mode. In this example, the dream improvement mode is preceded by the sleep improvement mode. The dream improvement mode may also be initiated independently from the sleep improvement mode, for example when the user has opted for a combination with the sleep meditation mode only. The dream improvement mode is initiated (step 301) when the control unit 5 detects, based on the signals from the one or more brainwave sensors 41, 42, 43, that the user is in the REM sleep stage, while one or more of the body vital sensors 44, 45, 46 reflect body vitals that distinguish the REM sleep stage from being awake, e.g. an increased heart rate that may have an irregular rhythm, an increased body temperature and a paralyzed body (step 303). Optionally, this step may be preceded by a check of the minimum sleep time S2 (if not already performed at step 214 of the sleep improvement mode, see FIG. 7) to ensure that the user has sufficient sleep before trying to obtain lucid dreaming (step 302). If the minimum sleep time S2, see FIG. 5, has not been reached, the dream improvement mode will not continue to the next step until the minimum sleep time S2 has been reached. Hence, the dream improvement mode may skip one or more REM sleep stages before actually continuing to the next step.

When one or more of the epochs E are scored as a REM sleep stage, the control unit 5 controls one or more of the one or more stimulus emitters 71-75 to emit the lucid dream inducing stimuli (step 304). The control unit 5 continues to receive signals representative of the brainwaves from the one or more brainwave sensors 41, 42, 43 and is arranged for detecting bursts of brainwave frequencies higher than the brainwave frequencies detected and stored in the memory 6 when the user was still awake, e.g. at the start of the sleep meditation mode. For example, the bursts of brainwave frequencies may be higher than 30 Hz whereas at the start of the sleep meditation mode, the control unit 5 registered normal activity with brainwaves in the range of 15 to 25 Hz in the Beta spectrum. These higher than awake brainwave frequency bursts can be an indication that the user has attained lucidity in a dream, i.e. the user recognizes the cues caused by the lucid dream inducing stimuli as anomalies in the dream and is becoming aware of dreaming (step 305). In this exemplary embodiment, the one or more stimulus emitters 71-75 continue to emit these lucid dream inducing stimuli until the bursts of relatively high brainwave frequencies are detected or when a predetermined or preprogrammed lucid dream cues timer has run out (step 306). The control unit 5 then ends the dream improvement mode (step 307).

FIG. 9 shows a flow chart of the wake up mode. The wake up mode can be enabled by the user before going to sleep by setting a wake up window in which the user wants to be woken up. As shown in FIG. 5, the wake up window is defined by a start time T1, being the earliest time at which the user wants to be woken up, and an end time T2, being the latest time at which the user needs to be woken up. Having a wake up window rather than a single, fixed alarm time enables the sleep improvement device 1 to wait for the most appropriate time to wake up the user. Waking the user in the NREM3 sleep stage can result in a groggy feeling. The best moment to wake the user is typically when the user is in the NREM2 sleep stage. Waking the user gradually from the NREM2 sleep stage will make the user feel refreshed.

As shown in FIG. 9, when the wake up mode is set up by the user (step 401), the control unit 5 will initiate the wake up mode when the start time T1 of the wake up window has been reached (step 402) and will determine, based on the brainwave signals from the one or more brainwave sensors 41, 42, 43 and/or the body vital signals from the one or more body vital sensors 44, 45, 46, the score of the last epoch E (step 403). When the last epoch E is scored as a NREM3 sleep stage and the end time T2 of the wake up window has not been reached, the control unit 5 will continue to monitor whether the user reaches the NREM2 sleep stage within the wake up window (step 404). When one or more of the epochs E are scored as a NREM2 sleep stage at the start time T1 of the wake up window or one or more of the epochs E are scored as a NREM2 sleep stage at any time during the wake up window, or when the end time T2 of the wake up window has been reached the control unit 5 will control one or more of the one or more stimulus emitters 71-75 to emit preset alarm stimuli (step 405). The alarm stimuli may be introduced gradually or in steps, e.g. by slowly increasing the volume and/or the intensity. Meanwhile, the control unit 5 continues to receive signals from the one or more brainwave sensors 41, 42, 43 and/or the one or more body vital sensors 44, 45, 46 to determine whether the user is now awake and repeats the alarm stimuli if the user is not yet awake (step 406). This is the end of the wake up mode (step 407).

The alarm stimuli can be set by the user. Alarm stimuli may comprise one or more stimuli of the group comprising: simulated natural sunlight, simulated natural sounds, tactile stimulus, the aroma of fresh cut grass, etc. Using the connectivity—if available—external smart home applications, such as smart speakers, smart lighting and smart scented candles may be used as further alarm stimuli.

As an optional feature, the sleep improvement device 1 according to the present invention can improve the perceived balance of the audio volume between the left ear and the right ear. When the user sleeps on one side, one of the speakers 73, 74 may be pressed against the user's head harder than the other speaker 73, 74. This can cause an annoying perception of unbalanced volume levels between the left ear and the right ear. To solve this, the control unit 5 can track the user's head position during sleep with the body movement sensor 44 and can control the volume of left speaker 73 and the right speaker 74 such that user perceives balanced audio stimuli between the left ear and the right ear, respectively.

As a further optional feature, the control unit 5 of the sleep improvement device 1 according to the present invention can detect snoring using the signals from the microphone 47. The control unit 5 can then control the audio stimulus emitters 73, 74, e.g. the speakers 73, 74, to emit phase reversed audio to mask or cancel out the snoring noise. It can also control one or more of the one or more stimulus emitters 71-75 to emit sleep position correcting stimuli to try and cause a change in sleeping position of the user. The control unit 5 can for example control the tactile stimulus emitter 75 to emit a short tactile stimulus that could be experienced by the user as a nudge. The control unit 5 continues to monitor the brainwave signals from the one or more brainwave sensors 41, 42, 43 and/or the body vital signals from the one or more body vital sensors 44, 45, 46 during each epoch E and scores each epoch E to make sure that the user is not unintentionally woken up.

It is to be understood that the above description is included to illustrate the operation of the preferred embodiments and is not meant to limit the scope of the invention. From the above discussion, many variations will be apparent to one skilled in the art that would yet be encompassed by the scope of the present invention.

For example, the sleep improvement device 1 could be used in a more general manner for facilitating power naps and general meditation, light therapy and health tracking. In these applications, the one or more brainwave sensors 41, 42, 43 and the one or more body vital sensors 44, 45, 46 could be used for the opposite purpose, e.g. to determine when the user unintentionally falls asleep and to prevent said falling asleep by emitting appropriate stimuli through one or more of the one or more stimulus emitters 71-75.

Moreover, the invention is also directed at a computer program product, storage medium or data carrier comprising instructions for causing the sleep improvement device 1 to execute the aforementioned method.

LIST OF REFERENCE NUMERALS 1 sleep improvement device
2 housing
3 band
41 first brainwave sensor
42 second brainwave sensor
43 third brainwave sensor
44 body movement sensor
45 heart rate sensor
46 body temperature sensor
47 microphone
5 control unit
6 memory
71 left visual stimulus emitter
72 right visual stimulus emitter
73 left audio stimulus emitter
74 right audio stimulus emitter
75 tactile stimulus emitter
81 communication module
82 external smart device
9 user's head
A Alpha brainwave
B Beta brainwave
D Delta brainwave
E epoch
S1 minimum deep sleep time
S2 minimum sleep time
T Theta brainwave
T1 start time
T2 end time
AW awake with eyes open
REM Rapid Eye Movement sleep stage
NREM1 first stage Non-Rapid Eye Movement
NREM2 second stage Non-Rapid Eye Movement
NREM3 third stage Non-Rapid Eye Movement
101 initiate sleep meditation mode
102 emit relaxing stimuli
103 brainwaves within training range?
104 emit training stimuli
105 epoch scored as NREM1 sleep stage?
106 sleep meditation timer reached?
107 fade out or turn off training stimuli
108 end of sleep meditation mode
201 initiate sleep improvement mode
202 end of dream improvement mode?
203 end of sleep meditation mode?
204 emit relaxing stimuli
205 epoch scored as NREM1 sleep stage?
206 emit sleep inducing stimuli
207 epoch scored as NREM2 sleep stage?
208 fade out or turn off relaxing stimuli
209 epoch scored as NREM3 sleep stage?
210 turn off relaxing stimuli
211 minimum deep sleep timer reached?
212 fade out or turn off sleep inducing stimuli
213 introduce white noise
214 epoch scored as REM sleep stage or awake, or wake up mode start time reached?
215 end of sleep improvement mode
216 rising slope of Delta brainwave?
217 emit amplitude enhancing stimuli
301 initiate dream improvement mode
302 minimum sleep timer reached?
303 epoch scored as REM sleep stage?
304 emit lucid dream inducing stimuli
305 attained lucidity in a dream or unintentionally awake?
306 lucid dream cues timer reached?
307 end of dream improvement mode
401 wake up mode set
402 start time reached?
403 epoch scored as NREM2 sleep stage?
404 end time reached?
405 emit alarm stimuli
406 epoch scored as awake?
407 end of wake up mode
Y yes
N no

The invention claimed is:

1. A sleep improvement device comprising one or more brainwave sensors for detecting brainwaves of a user, one or more body vital sensors for detecting body vitals of the user and a control unit that is operationally connected to said one or more brainwave sensors and said one or more body vital sensors for receiving and processing brainwave signals and body vital signals, respectively, wherein the control unit is arranged for monitoring the brainwave signals and/or the body vital signals during a plurality of epochs (E) and scoring sleep stages (AW, REM, NREM1, NREM2, NREM3) for each epoch (E), wherein the sleep improvement device is further provided with one or more stimulus emitters operationally connected to and controlled by the control unit, wherein the control unit is arranged for:
initiating a sleep meditation mode when the user is awake (AW), wherein in said sleep meditation mode the control unit is arranged for controlling one or more of the one or more stimulus emitters to emit relaxing stimuli, monitoring the brainwave signals during each epoch (E), determining when the user's brainwave frequencies for at least 20 percent of one or more of the epochs (E) are within a training range of 10 to 17 Hz and then controlling one or more of the one or more stimulus emitters to emit training stimuli; and
initiating a dream improvement mode when the control unit has scored one or more of the epochs (E) as a REM sleep stage (REM), wherein in said dream improvement mode the control unit is arranged for controlling one or more of the one or more stimulus emitters to emit lucid dream inducing stimuli corresponding to one or more of the training stimuli from the sleep meditation mode.

2. The improvement device according to claim 1, wherein the training range is 12 to 17 Hz.

3. The improvement device according to claim 1, wherein the training range is 13 to 16 Hz.

4. The improvement device according to claim 1, wherein the control unit is arranged for initiating a sleep improvement mode when the control unit has scored one or more of the epochs (E) as a NREM1 sleep stage (NREM1), wherein in said sleep improvement mode the control unit is arranged for controlling one or more of the one or more stimulus emitters to emit sleep inducing stimuli.

5. The improvement device according to claim 4, wherein the sleep inducing stimuli comprise brainwave entrainment stimuli, preferably binaural beats.

6. The improvement device according to claim 4, wherein the control unit is arranged for fading out or turning off the relaxing stimuli when the control unit has scored one or more of the epochs (E) as a NREM2 sleep stage (NREM2).

7. The improvement device according to claim 4, wherein the control unit is arranged for controlling one or more of the one or more stimulus emitters to introduce white noise when the control unit has scored one or more of the epochs (E) as a NREM3 sleep stage (NREM3).

8. The improvement device according to claim 7, wherein the control unit is provided with a deep sleep timer that adds up a deep sleep time of the epochs (E) that are scored as a NREM3 sleep stage (NREM3), wherein the control unit is arranged for fading out or turning off the sleep inducing stimuli when the control unit has determined that a predefined minimum deep sleep time (S1) has been reached.

9. The improvement device according to claim 7, wherein the control unit is provided with a deep sleep timer that adds up a deep sleep time of the epochs (E) that are scored as a NREM3 sleep stage (NREM3), wherein the control unit is arranged for introducing the white noise only after a predefined minimum deep sleep time (S1) has been reached.

10. The improvement device according to claim 4, wherein in the NREM3 sleep stages (NREM3), the user predominantly has brainwaves in the Delta frequency spectrum, wherein in said sleep improvement mode, the control unit is arranged for recognizing a rising slope of a Delta brainwave and for controlling one or more of the one or more stimulus emitters to emit amplitude enhancing stimuli during said rising slope.

11. The improvement device according to claim 10, wherein the amplitude enhancing stimuli comprise short audio stimuli and/or tactile stimuli.

12. The improvement device according to claim 1, wherein the control unit is provided with a sleep timer that adds up sleep time that the user is asleep from the first epoch (E) that is scored as a NREM1 sleep stage, wherein the control unit is arranged for emitting the lucid dream inducing stimuli only after a predefined minimum sleep time (S2) has been reached.

13. The improvement device according to claim 1, wherein the control unit is arranged for determining the brainwave frequencies of the user at the start of the sleep mentation mode and/or when the user was still awake, wherein in the dream improvement mode the control unit is arranged for detecting bursts of brainwave frequencies higher than the brainwave frequencies detected at the start of the sleep meditation mode and/or when the user was still awake.

14. The improvement device according to claim 13, wherein the control unit is arranged to control the one or more stimulus emitters to stop emitting the lucid dream inducing stimuli when said bursts of high brainwave frequencies are detected.

15. The improvement device according to claim 1, wherein the control unit is programmed with a wake up window having a start time (T1) and an end time (T2), wherein the control unit is arranged for initiating a wake up mode when the start time (T1) has been reached, wherein in said wake up mode the control unit is arranged for determining the sleep stage score (AW, REM, NREM1, NREM2, NREM3) of the last epoch (E) and for controlling one or more of the one or more stimulus emitters to emit alarm stimuli when the last epoch (E) is scored as a NREM2 sleep stage or when the end time (T2) has been reached.

16. The improvement device according to claim 1, wherein the one or more stimulus emitters comprises one or more stimulus emitters selected from the group consisting of visual stimulus emitters, audio stimulus emitters, tactile stimulus emitters and olfactory stimulus emitters.

17. The improvement device according to claim 1, wherein the one or more body vital sensor comprises one or more body vital sensor selected from the group consisting of a body movement sensor, a heart rate sensor and a body temperature sensor.

18. The improvement device according to claim 1, wherein the one or more stimulus emitters comprise a left speaker and a right speaker which are arranged to be placed at or near the user's left ear and right ear, respectively, and wherein the one or more body vital sensors comprise a body movement sensor, wherein the control unit is arranged for tracking the user's head position based on the body vital signals from the body movement sensor and for adjusting the volume of the left speaker and the right speaker based on the user's head position.

19. The improvement device according to claim 1, wherein the sleep improvement device is provided with a communication module to connect to one or more smart external devices that control the ambient conditions, wherein the control unit is arranged for controlling one or more of said smart external devices to adjust the ambient conditions based on the brainwave signals from the one or more brainwave sensors and/or the body vital signals from the one or more body vital sensors.

20. A method for improving sleep using the sleep improvement device according to claim 1, wherein the method comprises the steps of:
  initiating a sleep meditation mode when the user is awake (AW), in said sleep meditation mode emitting relaxing stimuli, monitoring the brainwave signals during each epoch (E), determining when the user's brainwave frequencies for at least 20 percent of one or more of the epochs (E) are within a training range of 10 to 17 Hz and then emitting training stimuli; and
  initiating a dream improvement mode when one or more of the epochs (E) are scored as a REM sleep stage (REM) and in said dream improvement mode emitting lucid dream inducing stimuli corresponding to one or more of the training stimuli from the sleep meditation mode.

21. The method according to claim 20, wherein the method further comprises the steps of initiating a sleep improvement mode when one or more of the epochs (E) are scored as a NREM1 sleep stage (NREM1) and in said sleep improvement mode emitting sleep inducing stimuli.

22. The method according to claim 20, wherein the method further comprises the step of introducing white noise when one or more of the epochs (E) are scored as a NREM3 sleep stage (NREM3).

23. The method according to claim 20, wherein in the NREM3 sleep stages (NREM3), the user predominantly has brainwaves in the Delta frequency spectrum, wherein the method further comprises the step of emitting amplitude enhancing stimuli during a rising slope of a Delta brainwave.

24. The method according to claim 20, wherein the method further comprises the steps of setting a wake up window having a start time (T1) and an end time (T2), initiating a wake up mode when the start time (T1) has been reached, in said wake up mode determining the sleep stage score (AW, REM, NREM1, NREM2, NREM3) of the last epoch (E) and emitting alarm stimuli when the last epoch (E) is scored as a NREM2 sleep stage or when the end time (T2) has been reached.

25. The method according to claim 20, wherein the method comprises the step of adjusting the ambient conditions based on the brainwaves and/or body vitals of the user.

26. A data carrier comprising instructions for causing the sleep improvement device, according to claim 1 to execute a method for improving sleep using the sleep improvement device (1), wherein the method comprises the steps of:
- initiating a sleep meditation mode when the user is awake (AW), in said sleep meditation mode emitting relaxing stimuli, monitoring the brainwave signal during each epoch (E), determining when the user's brainwave frequencies for at least 20 percent of one or more of the epochs (E) are within a training range of 10 to 17 Hz and then emitting training stimuli; and
- initiating a dream improvement mode when one or more of the epochs (E) are scored as a REM sleep stage (REM) and in said dream improvement mode emitting lucid dream inducing stimuli corresponding to one or more of the training stimuli from the sleep meditation mode.

\* \* \* \* \*

UNITED STATES PATENT AND TRADEMARK OFFICE
CERTIFICATE OF CORRECTION

PATENT NO.        : 10,532,183 B2
APPLICATION NO.   : 15/697268
DATED             : January 14, 2020
INVENTOR(S)       : Samir Sopan Raut et al.

It is certified that error appears in the above-identified patent and that said Letters Patent is hereby corrected as shown below:

Claim 13, Column 17, Line 44 "mentation" should be --meditation--

Signed and Sealed this
Seventh Day of April, 2020

Andrei Iancu
*Director of the United States Patent and Trademark Office*